(12) United States Patent  
Lin

(10) Patent No.: US 9,427,569 B2  
(45) Date of Patent: Aug. 30, 2016

(54) STRUCTURE OF ARTIFICIAL ELECTRONIC RETINA

(71) Applicant: Po-Kang Lin, Taipei (TW)

(72) Inventor: Po-Kang Lin, Taipei (TW)

( * ) Notice: Subject to any disclaimer, the term of this patent is extended or adjusted under 35 U.S.C. 154(b) by 0 days.

(21) Appl. No.: 14/714,343

(22) Filed: May 18, 2015

(65) Prior Publication Data

US 2015/0246220 A1    Sep. 3, 2015

Related U.S. Application Data

(63) Continuation-in-part of application No. 13/467,915, filed on May 9, 2012, now abandoned.

(51) Int. Cl.
*A61N 1/05* (2006.01)
*A61N 1/36* (2006.01)
*A61N 1/375* (2006.01)
*B82Y 30/00* (2011.01)

(52) U.S. Cl.
CPC ......... *A61N 1/0543* (2013.01); *A61N 1/36046* (2013.01); *A61N 1/3758* (2013.01); *B82Y 30/00* (2013.01)

(58) Field of Classification Search
CPC ........ A61N 1/05; A61N 1/0543; A61N 1/36; A61N 1/36046; A61N 1/3758; B82Y 30/00
USPC ........................ 607/53, 54, 116; 623/6.63, 24
See application file for complete search history.

(56) References Cited

U.S. PATENT DOCUMENTS

| | | | | | |
|---|---|---|---|---|---|
| 4,628,933 | A | * | 12/1986 | Michelson | A61F 2/14 607/53 |
| 5,016,633 | A | * | 5/1991 | Chow | A61F 2/14 607/53 |
| 5,024,223 | A | * | 6/1991 | Chow | A61F 2/14 257/E27.133 |
| 5,397,350 | A | * | 3/1995 | Chow | A61F 9/00727 128/898 |
| 5,556,423 | A | * | 9/1996 | Chow | A61F 9/00727 128/898 |
| 5,800,530 | A | * | 9/1998 | Rizzo, III | A61F 2/1613 623/6.22 |
| 5,804,836 | A | * | 9/1998 | Heeger | H01L 27/307 257/103 |
| 5,815,608 | A | * | 9/1998 | Lange | G06K 9/78 382/312 |
| 5,844,292 | A | * | 12/1998 | Thierry | H01L 31/1055 257/458 |
| 5,873,901 | A | * | 2/1999 | Wu | A61F 2/14 128/898 |
| 5,895,415 | A | * | 4/1999 | Chow | A61F 9/08 607/116 |
| 5,935,155 | A | * | 8/1999 | Humayun | A61M 5/3213 607/54 |
| 6,201,234 | B1 | * | 3/2001 | Chow | H04B 10/032 250/214 A |
| 6,230,057 | B1 | * | 5/2001 | Chow | A61F 9/08 607/116 |

(Continued)

*Primary Examiner* — Christopher A Flory
(74) *Attorney, Agent, or Firm* — Lin & Associates Intellectual Property, Inc.

(57) ABSTRACT

A structure of an artificial electronic retina is disclosed, which includes an array of a plurality of photoelectric units, and each photoelectric unit includes one electronic photosensitive element, one microelectrode, one electronic circuit, and sidewalls surrounding the photoelectric unit, wherein the microelectrode is disposed on and electrically connected to the electronic photosensitive element, and the electronic circuit is disposed on the electronic photosensitive element adjacent to the sidewalls near the circumference of the electronic photosensitive element. A layer of a light-permeable conductive material is disposed on the electronic photosensitive element between the microelectrode and the electronic circuit, wherein the layer of the light-permeable conductive material is electrically connected to both the electronic photosensitive element and the microelectrode. Therefore, the input and output power of the electronic photosensitive element can be increased without reducing the photosensitive area of the electronic photosensitive element.

10 Claims, 3 Drawing Sheets

(56) References Cited

U.S. PATENT DOCUMENTS

| | | | | |
|---|---|---|---|---|
| 6,389,317 B1* | 5/2002 | Chow | A61F 9/08 | 607/54 |
| 6,755,530 B1* | 6/2004 | Loftus | A61F 9/08 | 351/200 |
| 6,976,998 B2* | 12/2005 | Rizzo | A61F 2/14 | 607/54 |
| 7,001,608 B2* | 2/2006 | Fishman | C12M 35/02 | 424/422 |
| 7,291,540 B2* | 11/2007 | Mech | H01L 21/76251 | 257/E21.567 |
| 7,338,522 B2* | 3/2008 | Greenberg | A61N 1/0543 | 607/116 |
| 7,478,910 B1* | 1/2009 | Lin | A61B 5/6821 | 351/219 |
| 8,000,804 B1* | 8/2011 | Wessendorf | A61N 1/0543 | 607/115 |
| 8,150,526 B2* | 4/2012 | Gross | A61N 1/36046 | 607/53 |
| 8,428,740 B2* | 4/2013 | Gefen | A61N 1/0543 | 607/53 |
| 8,706,243 B2* | 4/2014 | Gefen | A61F 2/14 | 607/53 |
| 8,734,513 B2* | 5/2014 | Wu | A61N 1/36046 | 607/54 |
| 2002/0099420 A1* | 7/2002 | Chow | A61F 9/08 | 607/54 |
| 2003/0014089 A1* | 1/2003 | Chow | A61F 9/0017 | 607/54 |
| 2003/0097165 A1* | 5/2003 | Krulevitch | A61N 1/0543 | 607/115 |
| 2004/0181265 A1* | 9/2004 | Palanker | A61N 1/36046 | 607/54 |
| 2005/0090874 A1* | 4/2005 | Wu | A61F 2/14 | 607/54 |
| 2006/0142818 A1* | 6/2006 | Chow | A61F 9/0017 | 607/53 |
| 2007/0142878 A1* | 6/2007 | Krulevitch | A61N 1/0543 | 607/54 |
| 2008/0086206 A1* | 4/2008 | Nasiatka | A61F 9/08 | 623/6.14 |
| 2008/0288067 A1* | 11/2008 | Flood | A61N 1/0543 | 623/6.63 |
| 2009/0210055 A1* | 8/2009 | Chang | A61F 9/08 | 623/6.63 |
| 2010/0204754 A1* | 8/2010 | Gross | A61N 1/36046 | 607/53 |
| 2010/0249877 A1* | 9/2010 | Naughton | B82Y 20/00 | 607/54 |
| 2011/0117703 A1* | 5/2011 | Eckhardt | H01L 23/481 | 438/118 |
| 2011/0172736 A1* | 7/2011 | Gefen | A61N 1/0543 | 607/54 |
| 2012/0041514 A1* | 2/2012 | Gross | A61N 1/36046 | 607/53 |
| 2012/0056074 A1* | 3/2012 | Tian | H01L 27/14603 | 250/208.1 |
| 2012/0056075 A1* | 3/2012 | Tian | H01L 27/14603 | 250/208.1 |
| 2012/0209350 A1* | 8/2012 | Taylor | A61N 1/0526 | 607/54 |
| 2012/0259410 A1* | 10/2012 | Gefen | A61F 2/14 | 623/6.11 |
| 2013/0023986 A1* | 1/2013 | Keller | A61F 9/08 | 623/6.63 |
| 2013/0304155 A1* | 11/2013 | Lin | A61N 1/0543 | 607/54 |
| 2014/0188222 A1* | 7/2014 | Gefen | A61F 2/14 | 623/6.11 |
| 2015/0209586 A1* | 7/2015 | Silva | A61L 27/18 | 607/54 |
| 2016/0066789 A1* | 3/2016 | Rogers | A61N 1/05 | 604/20 |

* cited by examiner

STRUCTURE OF ARTIFICIAL ELECTRONIC RETINA

CROSS-REFERENCE TO RELATED APPLICATION

This application is a continuation-in-part of U.S. patent application Ser. No. 13/467,915, filed on May 9, 2012, which is incorporated herewith by reference.

BACKGROUND OF THE INVENTION

1. Field of the Invention

The present invention relates to a structure of an artificial electronic retina for an ophthalmological medical apparatus.

2. The Prior Arts

Blindness is the most serious problem that could happen to human eyes. The mechanism of eyesight is very complicated and is still not fully understandable even with the advanced science nowadays. Therefore, the recovery of eyesight has been impossible.

Besides the functions of sensing light and transmitting signals, retina has functions of preliminary identification of the contour of objects by the complicated and precise image processing circuit. For congenital retina degeneration, there is still no effective medical treatment for it. If a patient suffers from retinitis pigmentosa, he or she will have night blindness starting from around 10 to 20 years old and resulted in imperfect eyesight. The patient will become blind around 40 to 50 years old and there is still no effective medical treatment for it. Potential remedies for retinitis pigmentosa include retinal transplantation, gene therapy, neurohormonal treatment and artificial electronic retina. Among these remedies, the artificial electronic retina plays an important role in ophthalmology because of its potential in massive production.

The design for the artificial electronic retina is mainly categorized into epi-retinal device, sub-retinal device, complete layered retinal device and optic nerve encapsulated device. In the epi-retina device, the electric signals are used to stimulate the ganglion cells to generate the action potential. In the sub-retinal device, the electric signals are used to stimulate the light receiving cells to generate the action potential, and to help the light receiving cells to restore their functions. The epi-retinal device and sub-retinal device are developed at a faster pace and the preliminary human experimental results have been obtained in the United States of America. By using the epi-retinal device and the sub-retinal device, the partial eyesight of patients who suffer from retinitis pigmentosa are able to be restored. The ultimate goal of researches for the sub-retinal device in Taiwan is to develop the full-thickness electronic retina. Currently, the in vivo and in vitro tests have been performed to prove that the electronic retina can generate the recordable electrophysiological responses with the stimulation of light.

The artificial electronic retina is a bioelectronic device in which the electronic photosensitive elements are used to replace the retinal photosensitive cells, and the electronic photosensitive elements can stimulate the remnant optic nerve cells. Therefore, the eyesight can be restored by the electronic signals induced by the transmitted light. Similar devices can be implanted in the cerebrum to stimulate the cerebral cortex to generate eyesight. However, the eyesight system is complicated and huge, and its mechanism is still not fully understandable. Currently, the implantable artificial electronic retina is being emphasized the most in research and development.

The epi-retinal device is currently being developed the most successfully. The remnant ganglion cells of a patient suffered from retinitis pigmentosa are electrically stimulated by the arrays of microelectrodes disposed on the retina (i.e. by the vitreous body). The electrodes are simply the stimulating devices, and the signals and power supply are transmitted to the electrodes directly or indirectly via the wires, the infrared rays or the radio-frequency electric waves. The in vitro electronic photosensitive elements (e.g. CCD) can be incorporated with the suitable lens and with the integrated electronic visual circuits to form a device similar to the glasses. The signals and power supply are output simultaneously and are transmitted to the multiple arrays of microelectrodes on the retina. The epi-retinal device is used by many research institutions because it can be straightforwardly designed, developed and manufactured, and can be tested in vivo more easily.

The sub-retinal device can be used to replace the photosensitive cells on the ectoretina, and its design is simple. Because the sub-retinal device is disposed under the retina, it has the advantage that it is easy to be fixed. Furthermore, most retinal diseases are located on the ectoretina instead of the entorretina, and thereby the design of the sub-retinal device is suitable for applying to the clinical diseases. For patients suffered from retinal detachment, even though the retina can be attached back after a successful surgery, the photosensitive cells are usually dead and the eyesight cannot be restored. The sub-retinal device is capable of replacing the damaged photosensitive cells.

The sub-retinal device is used with the corresponding electronic visual circuits to simulate the collaborated functions of the photosensitive cells, horizontal cells, bipolar cells, amacrine cells and ganglion cells progressively. The sub-retinal device can be designed according to the various retinal diseases.

As humans are exploring and trying to comprehend the visual mechanism of the retina, the artificial electronic retina will be used for simulating the functions of the full-thickness retina in the future based on the improvement made on the research. Therefore, the problems of the retinal diseases can be solved, and even the healthy retina can be replaced, and inconceivable eyesight can be developed. The artificial electronic retina has the commercial, industrial and military potential, and is a major project developed by the advanced countries.

Currently, an artificial electronic retina comprises an array of photoelectric units composed of a plurality of electronic photosensitive elements and a plurality of microelectrodes. One microelectrode of each photoelectric unit is electrically connected to one electronic photosensitive element. Typically, the microelectrode is disposed at the center of the electronic photosensitive element, and an electronic circuit is disposed near the circumference of the electronic photosensitive element. The electronic photosensitive element is similar to the CMOS (complementary metal-oxide-semiconductor) or CCD (charge-coupled device) of the digital camera. After the artificial electronic retina is installed in the eyeball, an electric current is conducted through the array of microelectrodes to stimulate the nerve cells and to activate the electronic photosensitive elements, and thereby the images of light are formed on the photosensitive area of the electronic photosensitive elements. The electric current is then flowed back to the electronic circuits. Based on theories and practices, the output power of the microelectrodes is directly proportional to the effects of stimulating the nerve cells and activating the electronic photosensitive elements. Because the bigger the output power, the bigger the size of the microelectrodes is, so that more areas of the electronic photosensitive elements are covered by the microelectrodes. As a result, the photosensitive efficiency is reduced. Therefore, the input and output power of electric current conducted through the conventional artificial electronic retina cannot be enhanced by increasing the size of the microelectrodes.

SUMMARY OF THE INVENTION

An objective of the present invention is to provide a structure of an artificial electronic retina, which can increase the photosensitive efficiency by increasing the input and output power of the electronic photosensitive elements without affecting the amount of light entered.

In the array of the photoelectric units of the artificial electronic retina of the present invention, a light-permeable conductive material is disposed on and electrically connected to the electronic photosensitive element of each photoelectric unit, and the light-permeable conductive material is also electrically connected to the microelectrodes. Therefore, the input and output power of the electronic photosensitive elements can be increased, and the photosensitive efficiency can be increased without reducing the photosensitive area of the electronic photosensitive element.

In order to achieve the above objective, the present invention provides a structure of an artificial electronic retina, which comprises an array of a plurality of photoelectric units, each photoelectric unit including one electronic photosensitive element, one microelectrode, and one electronic circuit, the microelectrode being disposed on and electrically connected to the electronic photosensitive element, the electronic circuit being disposed on the electronic photosensitive element near the circumference, characterized in that: a layer of a light-permeable conductive material being disposed on and electrically connected to the electronic photosensitive element, wherein the layer of the light-permeable conductive material is also electrically connected to the microelectrode.

The light-permeable conductive material used in the present invention can be a conductive biomaterial, such as indium tin oxide, carbon nanotube, or graphene.

The light-permeable conductive material of the present invention can have a light-focusing structure to increase the amount of light entering into the electronic photosensitive element after passing through the light-permeable conductive material.

The light-permeable conductive material of the present invention can have an electricity-discharging structure to increase the input and output power of the electronic photosensitive element after the electric current has passed through the light-permeable conductive material.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
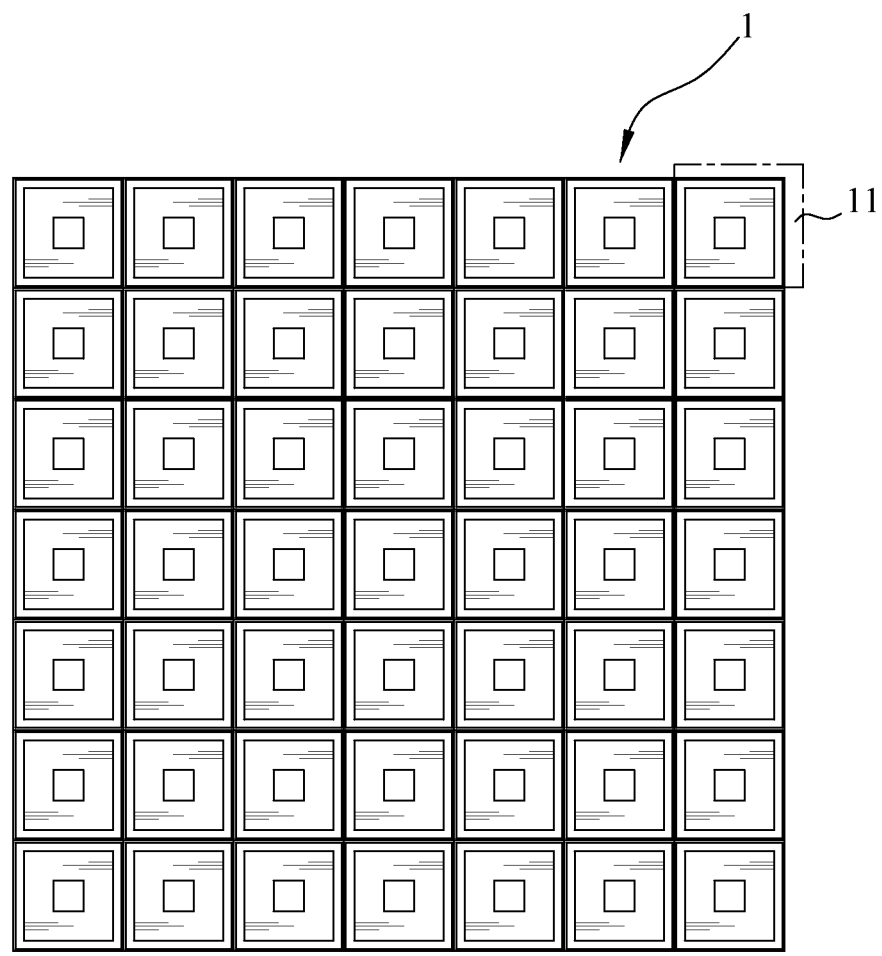
FIG. 1 is a top view of an array of the photoelectric units of an artificial electronic retina of the present invention.
Figure 2:
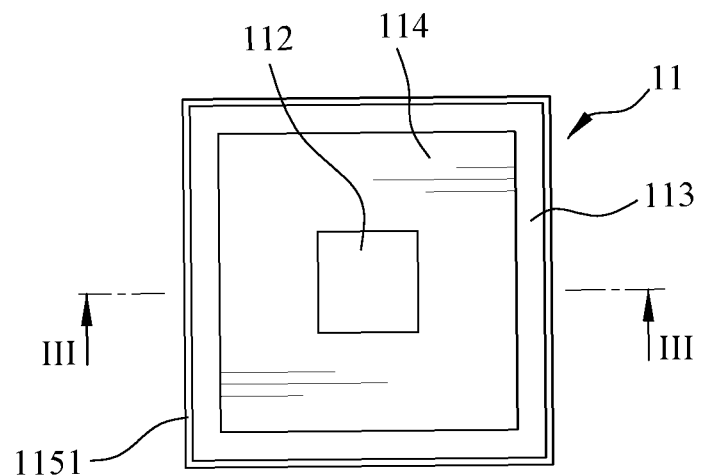
FIG. 2 is a top view of a photoelectric unit of the present invention.
Figure 3:
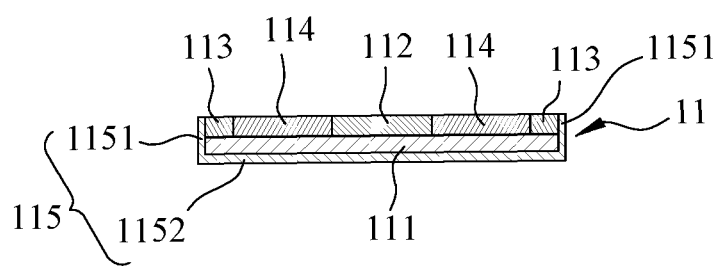
FIG. 3 is a cross-sectional view of FIG. 2 taken along line III-III.

FIG. 1 is a top view of an array of the photoelectric units of an artificial electronic retina of the present invention. The artificial electronic retina comprises a photoelectric unit array 1 composed of a plurality of photoelectric units 11. FIG. 2 is a top view of one single photoelectric unit 11. FIG. 3 is a cross-sectional view of the photoelectric unit 11 taken along line III-III of FIG. 2. Each of the photoelectric units 11 comprises an electronic photosensitive element 111, a microelectrode 112, an electronic circuit 113, and a base 115 including sidewalls 1151 and a bottom wall 1152. The sidewalls 1151 are formed around the photoelectric unit 11 to form a chamber with the bottom wall 1152. The microelectrode 112 is disposed on a top surface of the electronic photosensitive element 111 and electrically connected to the electronic photosensitive element 111. The electronic circuit 113 is disposed on the top surface of the electronic photosensitive element 111 immediately adjacent to the sidewalls 1151 near the circumference of the electronic photosensitive element 111. A layer of light-permeable conductive material 114 is further disposed on the top surface of the electronic photosensitive element 111.

As shown in the top view of FIG. 2, each photoelectric unit 11 is substantially square with sidewalls 1151 surrounding the photoelectric unit 11. The photoelectric units 11 are arranged in an array with sidewalls 1151 of each photoelectric unit 11 abutting sidewalls 1151 of the bases 115 of neighboring photoelectric units 11 as shown in FIG. 1. The layer of the light-permeable conductive material 114 is disposed in an independent manner on the top surface of the electronic photosensitive element 111 between the microelectrode 112 and the electronic circuit 113 in each photoelectric unit 11 and surrounding the microelectrode 112. The inner surface of the layer of the light-permeable conductive material 114 abuts against the outer surface of the microelectrode 112 as shown in FIGS. 2 and 3. The electronic photosensitive element 111, the microelectrode 112, the layer of the light-permeable conductive material 114 and the electronic circuit 113 are received in the chamber formed by the sidewalls 1151 and the bottom wall 1152. The bottom surface of the electronic photosensitive element 111 abuts against the bottom wall 1152 of the base 115. Both the outer surface of the electronic photosensitive element 111 and the outer surface of the electronic circuit 113 abut against the inner surfaces of the sidewalls 1151 of the base 115.

As shown in FIGS. 2 and 3, the electronic circuit 113 also keeps the light-permeable conductive material 114 away from the sidewalls 115 of the photoelectric unit 11. The light-permeable conductive material 114 is electrically connected to both the electronic photosensitive element 111 and the microelectrode 112. In one preferred embodiment of the present invention, based on the consideration of reducing the discomfort to the minimum after the installation of the artificial electronic retina in the human eyeball, the light-permeable conductive material 114 is made of a biomaterial, for examples indium tin oxide, carbon nanotube or graphene, which can be compatible with the human eyeball.

After the photoelectric unit array 1 is manufactured by standard semiconductor manufacturing processes, the light-permeable conductive material 114 made of indium tin oxide, carbon nanotube or graphene can be disposed on the surface of the electronic photosensitive element 111 by, for example, vacuum evaporation or sputtering, and electrically connected to both the electronic photosensitive element 111 and the microelectrode 112. The thickness of the light-permeable conductive material 114 can be adjusted within the range of 0.01 to 10000 nanometers based on the practical requirements. Preferably, the light transmittance of the light-permeable conductive material 114 is above 90%.

According to the structure of the artificial electronic retina, the microelectrode 112 is connected to a power source, and a suitable amount of electric current is conducted through the light-permeable conductive material 114 via the microelectrode 112, and then the electric current is input into the electronic photosensitive element 111 and then flowed back to the electronic circuit 113. Because the light-permeable conductive material 114 is in contact with the electronic photosensitive element 111 between the microelectrode 112 and the electronic circuit 113, the electric current can be input into every part of the electronic photosensitive element 111. Therefore, the input and output values of the electric current can be enhanced. However, the photosensitive area of the electronic photosensitive element 111 remains the same. Even the area of the microelectrode 112 can be reduced, and consequently the photosensitive area of the electronic photosensitive element 111 is increased. As a result, the amount of light entered and the photosensitive efficiency can be enhanced.

Figure 4:
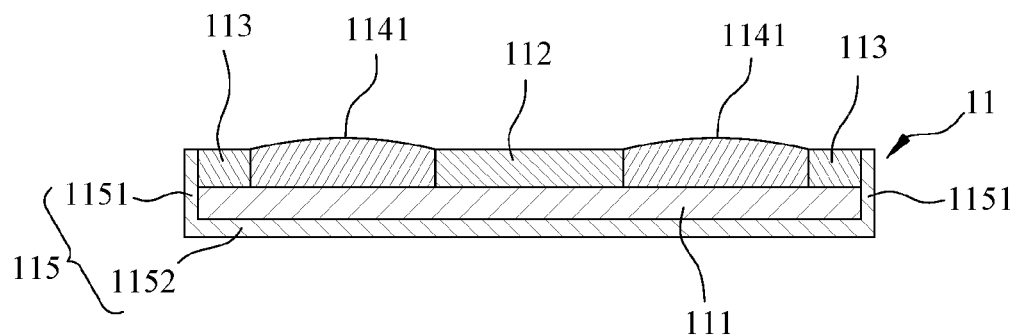
FIG. 4 is a cross-sectional view of a protruded arc-shaped surface formed on a light-permeable conductive material according to one embodiment of the present invention.
Figure 5:
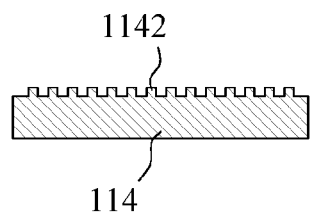
FIG. 5 is a cross-sectional view of the protruding portions formed on the surface of the layer of the light-permeable conductive material for focusing light according to one embodiment of the present invention.

In order to further enhance the amount of light transmitted through the light-permeable conductive material 114, a light focusing structure can be disposed on the light-permeable conductive material 114. As shown in FIG. 4, the light-permeable conductive material 114 can have a protruded arc-shaped surface 1141. Therefore, the light-permeable conductive material 114 can focus light just like a convex lens, and the contact area between the microelectrode 112 and the retina can be increased. As shown in FIG. 5, a plurality of protruding portions 1142 are formed on the surface of the light-permeable conductive material 114. The protruding portions 1142 can be in any shapes such as indention, wavy or triangular, etc., which can refract and focus light. Thereby, the light can be more focused and the amount of transmitted light can enhanced after passing through the light-permeable conductive material 114.

Figure 6:
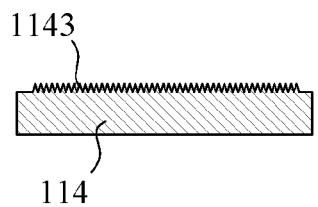
FIG. 6 is a cross-sectional view of the acute protruding portions formed on the surface of the layer of the light-permeable conductive material for focusing light and point discharging according to one embodiment of the present invention.

Furthermore, as shown in FIG. 6, a structure which discharges electricity can be further disposed on the surface of the light-permeable conductive material 114. For example, a plurality of acute protruding portions 1143 is formed on the surface of the light-permeable conductive material 114. Therefore, after the electric current is conducted through the light-permeable conductive material 114 via the microelectrode 112, the point discharge occurred at the acute protruding portions 1143. Therefore, the power of electric current input into the electronic photosensitive element 111 can be enhanced.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A structure of an artificial electronic retina comprising an array of a plurality of photoelectric units, each photoelectric unit including:
    an electronic photosensitive element;
    a microelectrode disposed on a top surface of the electronic photosensitive element and electrically connected to the electronic photosensitive element;
    a layer of a light-permeable conductive material disposed in an independent manner on the top surface of the electronic photosensitive element in each photoelectric unit and surrounding the microelectrode, an inner surface of the layer of the light-permeable conductive material abutting against an outer surface of the microelectrode, and the layer of the light-permeable conductive material electrically connected to the microelectrode and the electronic photosensitive element;
    an electronic circuit disposed on the top surface of the electronic photosensitive element and surrounding the layer of the light-permeable conductive material, and an inner surface of the electronic circuit abutting against an outer surface of the layer of the light-permeable conductive material; and
    a base including sidewalls and a bottom wall, the sidewalls abutting against sidewalls of bases of neighboring photoelectric units and forming a chamber with the bottom wall;
    wherein the electronic photosensitive element, the microelectrode, the layer of the light-permeable conductive material and the electronic circuit are received in the chamber, a bottom surface of the electronic photosensitive element abuts against the bottom wall of the base, both an outer surface of the electronic photosensitive element and an outer surface of the electronic circuit abuts against inner surfaces of the sidewalls of the base.

2. The structure as claimed in claim 1, wherein the light-permeable conductive material is a conductive biomaterial.

3. The structure as claimed in claim 2, wherein the conductive biomaterial is indium tin oxide.

4. The structure as claimed in claim 2, wherein the conductive biomaterial is carbon nanotube.

5. The structure as claimed in claim 2, wherein the conductive biomaterial is graphene.

6. The structure as claimed in claim 1, wherein the light-permeable conductive material has a light-focusing structure.

7. The structure as claimed in claim 6, wherein the light-focusing structure has a protruded arc-shaped surface.

8. The structure as claimed in claim 6, wherein the light-focusing structure has a plurality of protruding portions formed on a surface of the light-permeable conductive material.

9. The structure as claimed in claim 1, wherein the light-permeable conductive material has an electricity-discharging structure.

10. The structure as claimed in claim 9, wherein the electricity-discharging structure has a plurality of acute protruding portions formed on a surface of the light-permeable conductive material for point discharging.

* * * * *